United States Patent
Goldwasser et al.

(10) Patent No.: US 9,241,614 B2
(45) Date of Patent: Jan. 26, 2016

(54) TOOLS FOR USE IN ESOPHAGUS

(75) Inventors: Benad Goldwasser, Tel Aviv (IL); Oz Cabiri, Macabim (IL); Yossi Gross, Moshav Mazor (IL); Shlomo Lewkowicz, Tivon (IL)

(73) Assignee: G.I. VIEW LTD., Ramat Gan (IL)

( * ) Notice: Subject to any disclaimer, the term of this patent is extended or adjusted under 35 U.S.C. 154(b) by 1744 days.

(21) Appl. No.: 11/997,684

(22) PCT Filed: Aug. 1, 2006

(86) PCT No.: PCT/IL2006/000890
§ 371 (c)(1),
(2), (4) Date: Jul. 3, 2009

(87) PCT Pub. No.: WO2007/015241
PCT Pub. Date: Feb. 8, 2007

(65) Prior Publication Data
US 2011/0092765 A1   Apr. 21, 2011

Related U.S. Application Data

(60) Provisional application No. 60/704,656, filed on Aug. 1, 2005.

(51) Int. Cl.
*A61B 1/04* (2006.01)
*A61B 1/00* (2006.01)
*A61B 5/06* (2006.01)
*A61B 5/00* (2006.01)
(Continued)

(52) U.S. Cl.
CPC .............. *A61B 1/04* (2013.01); *A61B 1/00147* (2013.01); *A61B 5/064* (2013.01); *A61B 5/6882* (2013.01); *A61B 10/0266* (2013.01); *A61B 10/0283* (2013.01); *A61B 10/04* (2013.01); *A61B 2010/0061* (2013.01)

(58) Field of Classification Search
CPC . A61B 1/00156; A61B 1/00082; A61B 1/041
See application file for complete search history.

(56) References Cited

U.S. PATENT DOCUMENTS 3,895,637 A   7/1975   Choy
3,924,625 A   12/1975  Peterson
(Continued)

FOREIGN PATENT DOCUMENTS

EP   0242428   10/1987
EP   0267446   5/1988
(Continued)

OTHER PUBLICATIONS

U.S. Appl. No. 60/607,986, filed Sep. 8, 2004.
(Continued)

*Primary Examiner* — Anhtuan T Nguyen
*Assistant Examiner* — Alexandra Newton
(74) *Attorney, Agent, or Firm* — Browdy and Neimark, PLLC

(57) ABSTRACT

Apparatus (10) is provided, including an elongate carrier (24), configured to be advanced through an esophagus (20) of a subject. An anchor member (30) is coupled to a distal end of the carrier, and configured to be mounted in a stomach (32) of the subject in a vicinity of a lower esophageal sphincter (LES) (34) of the subject. An imaging capsule (26) is configured to move with respect to the carrier when the anchor member is in the vicinity of the LES. Other embodiments are also described.

16 Claims, 3 Drawing Sheets

(51) Int. Cl.
*A61B 10/02* (2006.01)
*A61B 10/04* (2006.01)
*A61B 10/00* (2006.01)

(56) References Cited

U.S. PATENT DOCUMENTS

| | | | |
|---|---|---|---|
| 4,040,413 A | 8/1977 | Ohshiro et al. | |
| 4,066,070 A | 1/1978 | Utsugi et al. | |
| 4,077,610 A | 3/1978 | Masuda et al. | |
| 4,148,307 A | 4/1979 | Utsugi et al. | |
| 4,176,662 A | 12/1979 | Frazer | |
| 4,403,985 A | 9/1983 | Boretos | |
| 4,530,698 A | 7/1985 | Goldstein et al. | |
| 4,561,427 A | 12/1985 | Takada et al. | |
| 4,596,381 A | 6/1986 | Hamrick | |
| 4,690,131 A | 9/1987 | Lyddy, Jr. et al. | |
| 4,838,859 A | 6/1989 | Strassmann | |
| 4,971,034 A | 11/1990 | Doi et al. | |
| 4,976,524 A | 12/1990 | Chiba et al. | |
| 5,259,364 A | 11/1993 | Bob et al. | |
| 5,337,732 A | 8/1994 | Grundfest et al. | |
| 5,353,807 A | 10/1994 | DeMarco | |
| 5,364,353 A | 11/1994 | Corfitsen et al. | |
| 5,395,332 A | 3/1995 | Ressemann et al. | |
| 5,398,670 A | 3/1995 | Ortiz et al. | |
| 5,471,988 A | 12/1995 | Fujio et al. | |
| 5,509,371 A | 4/1996 | Phillips | |
| 5,571,114 A | 11/1996 | Devanaboyina | |
| 5,586,968 A | 12/1996 | Grundl et al. | |
| 5,604,531 A | 2/1997 | Iddan et al. | |
| 5,662,587 A | 9/1997 | Grundfest et al. | |
| 5,728,068 A | 3/1998 | Leone et al. | |
| 5,863,284 A | 1/1999 | Klein | |
| 5,879,325 A | 3/1999 | Lindstrom et al. | |
| 5,906,357 A | 5/1999 | Munson, Sr. | |
| 5,906,591 A | 5/1999 | Dario et al. | |
| 5,910,105 A | 6/1999 | Swain et al. | |
| 5,941,815 A | 8/1999 | Chang | |
| 5,984,860 A | 11/1999 | Shan | |
| 6,007,482 A | 12/1999 | Madni et al. | |
| 6,028,719 A | 2/2000 | Beckstead et al. | |
| 6,071,234 A | 6/2000 | Takada et al. | |
| 6,130,783 A | 10/2000 | Yagi et al. | |
| 6,157,018 A | 12/2000 | Ishiguro et al. | |
| 6,277,065 B1* | 8/2001 | Donofrio | 600/115 |
| 6,315,713 B1 | 11/2001 | Takada et al. | |
| 6,332,865 B1 | 12/2001 | Borody et al. | |
| 6,333,826 B1 | 12/2001 | Charles | |
| 6,341,044 B1 | 1/2002 | Driscoll, Jr. et al. | |
| 6,356,296 B1 | 3/2002 | Driscoll, Jr. et al. | |
| 6,373,642 B1 | 4/2002 | Wallerstein et al. | |
| 6,388,820 B1 | 5/2002 | Wallerstein et al. | |
| 6,422,989 B1 | 7/2002 | Hektner | |
| 6,424,377 B1 | 7/2002 | Driscoll, Jr. et al. | |
| 6,439,032 B1 | 8/2002 | Lehmann et al. | |
| 6,449,103 B1 | 9/2002 | Charles | |
| 6,459,451 B2 | 10/2002 | Driscoll, Jr. et al. | |
| 6,485,409 B1 | 11/2002 | Voloshin et al. | |
| 6,493,032 B1 | 12/2002 | Wallerstein et al. | |
| 6,503,192 B1 | 1/2003 | Ouchi et al. | |
| 6,517,477 B1 | 2/2003 | Wendlandt | |
| 6,527,705 B1 | 3/2003 | Ouchi et al. | |
| 6,537,206 B2 | 3/2003 | Takada et al. | |
| 6,597,520 B2 | 7/2003 | Wallerstein et al. | |
| 6,599,237 B1 | 7/2003 | Singh | |
| 6,611,282 B1 | 8/2003 | Trubko et al. | |
| 6,646,818 B2 | 11/2003 | Doi et al. | |
| 6,648,814 B2 | 11/2003 | Kim et al. | |
| 6,682,479 B1 | 1/2004 | Takahashi et al. | |
| 6,695,771 B2 | 2/2004 | Takada et al. | |
| 6,702,734 B2 | 3/2004 | Kim et al. | |
| 6,702,735 B2 | 3/2004 | Kelly et al. | |
| 6,704,148 B2 | 3/2004 | Kumata et al. | |
| 6,709,388 B1 | 3/2004 | Mosse et al. | |
| 6,719,684 B2* | 4/2004 | Kim et al. | 600/101 |
| 6,743,208 B1 | 6/2004 | Coyle | |
| 6,764,441 B2 | 7/2004 | Chiel et al. | |
| 6,786,864 B2 | 9/2004 | Matsuura et al. | |
| 6,800,056 B2 | 10/2004 | Tartaglia et al. | |
| 6,814,728 B2 | 11/2004 | Ouchi et al. | |
| 6,824,510 B2 | 11/2004 | Kim et al. | |
| 6,827,718 B2 | 12/2004 | Hutchins et al. | |
| 6,837,846 B2 | 1/2005 | Jaffe et al. | |
| 6,866,626 B2 | 3/2005 | Long et al. | |
| 6,869,393 B2 | 3/2005 | Butler et al. | |
| 6,911,005 B2 | 6/2005 | Ouchi et al. | |
| 6,932,323 B2 | 8/2005 | James | |
| 6,974,441 B2 | 12/2005 | Ravo et al. | |
| 7,056,283 B2 | 6/2006 | Baror et al. | |
| 2002/0012059 A1 | 1/2002 | Wallerstein et al. | |
| 2002/0072651 A1 | 6/2002 | Vilos | |
| 2002/0107478 A1 | 8/2002 | Wendlandt | |
| 2002/0109772 A1 | 8/2002 | Kuriyama et al. | |
| 2002/0109773 A1 | 8/2002 | Kuriyama et al. | |
| 2003/0000526 A1 | 1/2003 | Gobel | |
| 2003/0074015 A1 | 4/2003 | Nakao | |
| 2003/0083547 A1 | 5/2003 | Hamilton et al. | |
| 2003/0105386 A1 | 6/2003 | Voloshin et al. | |
| 2003/0120130 A1* | 6/2003 | Glukhovsky et al. | 600/109 |
| 2003/0153866 A1 | 8/2003 | Long et al. | |
| 2003/0168068 A1 | 9/2003 | Poole et al. | |
| 2003/0181788 A1 | 9/2003 | Yokoi et al. | |
| 2003/0191369 A1 | 10/2003 | Arai et al. | |
| 2003/0208219 A1 | 11/2003 | Aznoian et al. | |
| 2003/0214580 A1* | 11/2003 | Iddan | 348/81 |
| 2003/0225433 A1 | 12/2003 | Nakao | |
| 2004/0004836 A1 | 1/2004 | Dubuc | |
| 2004/0102681 A1 | 5/2004 | Gross | |
| 2004/0111010 A1 | 6/2004 | Nishiie | |
| 2004/0143161 A1 | 7/2004 | Baror et al. | |
| 2004/0199087 A1 | 10/2004 | Swain et al. | |
| 2004/0199088 A1 | 10/2004 | Bakos et al. | |
| 2004/0199196 A1 | 10/2004 | Ravo | |
| 2004/0204702 A1 | 10/2004 | Ziegler et al. | |
| 2004/0249247 A1 | 12/2004 | Iddan | |
| 2004/0260150 A1 | 12/2004 | Bernstein | |
| 2005/0036059 A1 | 2/2005 | Goldwasser | |
| 2005/0038317 A1 | 2/2005 | Ratnakar | |
| 2005/0038318 A1 | 2/2005 | Goldwasser | |
| 2005/0038319 A1 | 2/2005 | Goldwasser et al. | |
| 2005/0038335 A1 | 2/2005 | Gross et al. | |
| 2005/0085841 A1 | 4/2005 | Eversull et al. | |
| 2005/0095200 A1 | 5/2005 | Schwarzberg | |
| 2005/0107664 A1 | 5/2005 | Kalloo et al. | |
| 2005/0154278 A1 | 7/2005 | Cabiri et al. | |
| 2005/0154355 A1* | 7/2005 | Gross et al. | 604/232 |
| 2005/0154413 A1* | 7/2005 | Trabada et al. | 606/190 |
| 2005/0165272 A1 | 7/2005 | Okada et al. | |
| 2005/0197531 A1 | 9/2005 | Cabiri et al. | |
| 2005/0245788 A1* | 11/2005 | Gerber | 600/115 |
| 2010/0137686 A1 | 6/2010 | Meron et al. | |

FOREIGN PATENT DOCUMENTS

| | | |
|---|---|---|
| EP | 0659387 | 6/1995 |
| FR | 1465723 | 1/1967 |
| JP | 7313443 | 12/1995 |
| JP | 2006026344 | 2/2006 |
| WO | 0044275 | 8/2000 |
| WO | 01/68540 A2 | 9/2001 |
| WO | 02059676 | 8/2002 |
| WO | 02/075348 A2 | 9/2002 |
| WO | 03026272 | 3/2003 |
| WO | 03045487 | 6/2003 |
| WO | 03046830 | 6/2003 |
| WO | 03053225 | 7/2003 |
| WO | 2004010858 | 2/2004 |
| WO | 2004016299 | 2/2004 |

(56) References Cited

FOREIGN PATENT DOCUMENTS

| WO | 2004069057 | 8/2004 |
| WO | 2005065044 | 7/2005 |
| WO | 2005110186 | 11/2005 |
| WO | 2006025045 | 3/2006 |
| WO | 2006072928 | 7/2006 |

OTHER PUBLICATIONS

U.S. Appl. No. 60/571,438, filed May 14, 2004.
U.S. Appl. No. 60/652,049, filed Feb. 10, 2005.
U.S. Appl. No. 60/642,245, filed Jan. 6, 2005.
U.S. Appl. No. 60/680,074, filed May 11, 2005.
U.S. Appl. No. 60/704,656, filed Aug. 1, 2005.

* cited by examiner

TOOLS FOR USE IN ESOPHAGUS

CROSS-REFERENCES TO RELATED APPLICATIONS

The present application is the U.S. national phase application of PCT Application no. PCT/IL2006/000890 to Goldwasser et al., filed Aug. 1, 2006, which claims the benefit of U.S. Provisional Patent Application 60/704,656 to Goldwasser et al., filed Aug. 1, 2005, which is assigned to the assignee of the present patent application and is incorporated herein by reference. The International Application was published in English on Feb. 8, 2007 as WO 2007/015241 A2 under PCT Article 21(2).

FIELD OF THE INVENTION

The present invention relates generally to a pressure-propelled system, suitable for imaging body lumens, such as the esophagus.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like.

US Patent Application Publication 2005/0154355 to Gross et al., which is assigned to the assignee of the present application and is incorporated herein by reference, describes apparatus for use with a fluid pressure source. The apparatus includes an elongate carrier, adapted to be inserted through a proximal opening of a body lumen, and a distal piston head coupled to a distal portion of the carrier. The piston head is adapted to be in direct contact with a wall of the lumen when the carrier is inserted into the lumen, and to be advanced distally through the body lumen in response to pressure from the fluid pressure source.

The following references, which are incorporated herein by reference, may be of interest:

US Patent Application Publication 2004/0102681 to Gross
US Patent Application Publication 2005/0036059 to Goldwasser
US Patent Application Publications 2005/0038318 and 2005/0038319 to Goldwasser
US Patent Application Publication 2005/0038335 to Gross et al.
US Patent Application Publication 2005/0154278 to Cabiri et al.
PCT Publication WO 05/065044 to Cabiri et al.
U.S. Pat. No. 5,984,860 to Shan
U.S. Pat. No. 6,866,626 to Long et al.
U.S. Pat. No. 5,571,114 to Devanaboyina
U.S. Pat. No. 6,682,479 to Takahashi et al.
US Patent Application Publication 2004/0260150 to Bernstein
U.S. Pat. No. 6,709,388 to Mosse et al.
US Patent Application Publication 2005/0095200 to Schwarzberg
US Patent Application Publication 2005/0038317 to Ratnakar
U.S. Pat. No. 6,869,393 to Butler
U.S. Pat. No. 5,941,815 to Chang
U.S. Pat. No. 5,879,325 to Lindstrom et al.
U.S. Pat. No. 5,337,732 to Grundfest et al.
US Patent Application Publication 2003/0168068 to Poole and Young
US Patent Application Publication 2003/0105386 and U.S. Pat. No. 6,485,409 to Voloshin et al.
US Patent Application Publication 2002/0107478 to Wendlandt
U.S. Pat. No. 6,702,735 to Kelly
U.S. Pat. No. 5,259,364 to Bob, et al.
U.S. Pat. No. 4,403,985 to Boretos
U.S. Pat. No. 4,176,662 to Frazer
U.S. Pat. No. 4,148,307 to Utsugi
U.S. Pat. No. 5,906,591 to Dario et al.
U.S. Pat. No. 6,007,482 to Madni et al.
U.S. Pat. No. 5,662,587 to Grundfest et al.
U.S. Pat. No. 4,690,131 to Lyddy, Jr. et al.
U.S. Pat. No. 4,040,413 to Ohshiro
U.S. Pat. No. 6,503,192 to Ouchi
U.S. Pat. No. 6,814,728 to Ouchi
U.S. Pat. No. 6,911,005 to Ouchi et al.
US Patent Application Publication 2003/0083547 to Hamilton et al.
PCT Publication WO 04/069057 to Gobel
US Patent Application Publication 2003/0000526 to Gobel
PCT Publication WO 03/045487 to Gobel
U.S. Pat. No. 4,561,427 to Takada
U.S. Pat. No. 6,071,234 to Takada
U.S. Pat. No. 6,332,865 to Borody et al.

SUMMARY OF THE INVENTION

In some embodiments of the present invention, an imaging system is provided for examining an esophagus of a subject. The system comprises an elongate carrier coupled at a distal end thereof to an inflatable anchoring member. The anchoring member is inserted via the esophagus to a site in the stomach in a vicinity of a lower esophageal sphincter (LES), and inflated so as to anchor the distal end of the carrier. The system further comprises an imaging capsule configured to travel along the carrier distally and proximally in the esophagus (i.e., towards the stomach and towards the mouth, respectively). The imaging capsule comprises at least one imaging element, which is configured to image the esophagus.

In some embodiments of the present invention, the imaging capsule comprises a piston head, which is configured to form a pressure seal with a wall of the esophagus. Pressure from a fluid pressure source is applied to the area of the esophagus between the piston head and the anchoring member. The pressure causes the imaging capsule to travel proximally through the esophagus. Alternatively, the imaging capsule is withdrawn proximally using a wire.

There is therefore provided, in accordance with an embodiment of the invention, apparatus, including:

an elongate carrier, configured to be advanced through an esophagus of a subject;

an anchor member, coupled to a distal end of the carrier, and configured to be mounted in a stomach of the subject in a vicinity of a lower esophageal sphincter (LES) of the subject; and an imaging capsule, configured to move with respect to the carrier when the anchor member is in the vicinity of the LES.

In an embodiment, the capsule includes a sample collection unit, configured to sample fluid or tissue of the esophagus.

In an embodiment, the apparatus includes a sample collection unit coupled to the carrier and not an integral portion of the imaging capsule, wherein the collection unit is configured to sample fluid or tissue of the esophagus.

In an embodiment, the imaging capsule is shaped to define a bore thereof, and wherein the carrier is configured to pass through the bore to allow the imaging capsule to move with respect to the carrier.

In an embodiment, the anchor member includes an inflatable anchor member.

In an embodiment, the anchor member includes a non-inflatable anchor member, shown as one example 30n in FIG. 2.

There is further provided, in accordance with an embodiment of the invention, apparatus for use with a biologically-compatible-fluid pressure source, including:

an elongate carrier, configured to be advanced through an esophagus of a subject;

an inflatable anchor member, coupled to a distal end of the carrier, and configured to be mounted in a stomach of the subject in a vicinity of a lower esophageal sphincter (LES) of the subject, and to form a pressure seal upon inflation; and an imaging capsule, configured to travel along the carrier, the imaging capsule including:

an imaging element; and a piston head configured to:

form a pressure seal with a wall of the esophagus, and be advanced proximally through the esophagus in response to pressure from the fluid pressure source.

In an embodiment, the capsule includes a sample collection unit, configured to sample fluid or tissue of the esophagus.

In an embodiment, the apparatus includes a sample collection unit coupled to the carrier and not an integral portion of the imaging capsule, wherein the collection unit is configured to sample fluid or tissue of the esophagus.

There is still further provided, in accordance with an embodiment of the invention, a method, including:

advancing an elongate carrier through an esophagus of a subject;

mounting in a stomach of the subject in a vicinity of a lower esophageal sphincter (LES) of the subject an anchor member that is coupled to a distal end of the carrier; and moving a capsule with respect to the carrier when the anchor member is in the vicinity of the LES.

In an embodiment, moving the capsule includes moving an imaging capsule.

In an embodiment, moving the capsule includes moving a capsule that applies a treatment to the esophagus.

In an embodiment, the method includes sampling fluid or tissue of the esophagus by the capsule.

In an embodiment, the capsule is shaped to define a bore thereof, and including placing the carrier within the bore.

In an embodiment, mounting the anchor member includes inflating the anchor member when it is in the stomach.

In an embodiment, mounting the anchor member includes expanding the anchor member when it is in the stomach.

The present invention will be more fully understood from the following detailed description of embodiments thereof, taken together with the drawings, in which:

DETAILED DESCRIPTION OF EMBODIMENTS

Figure 1:
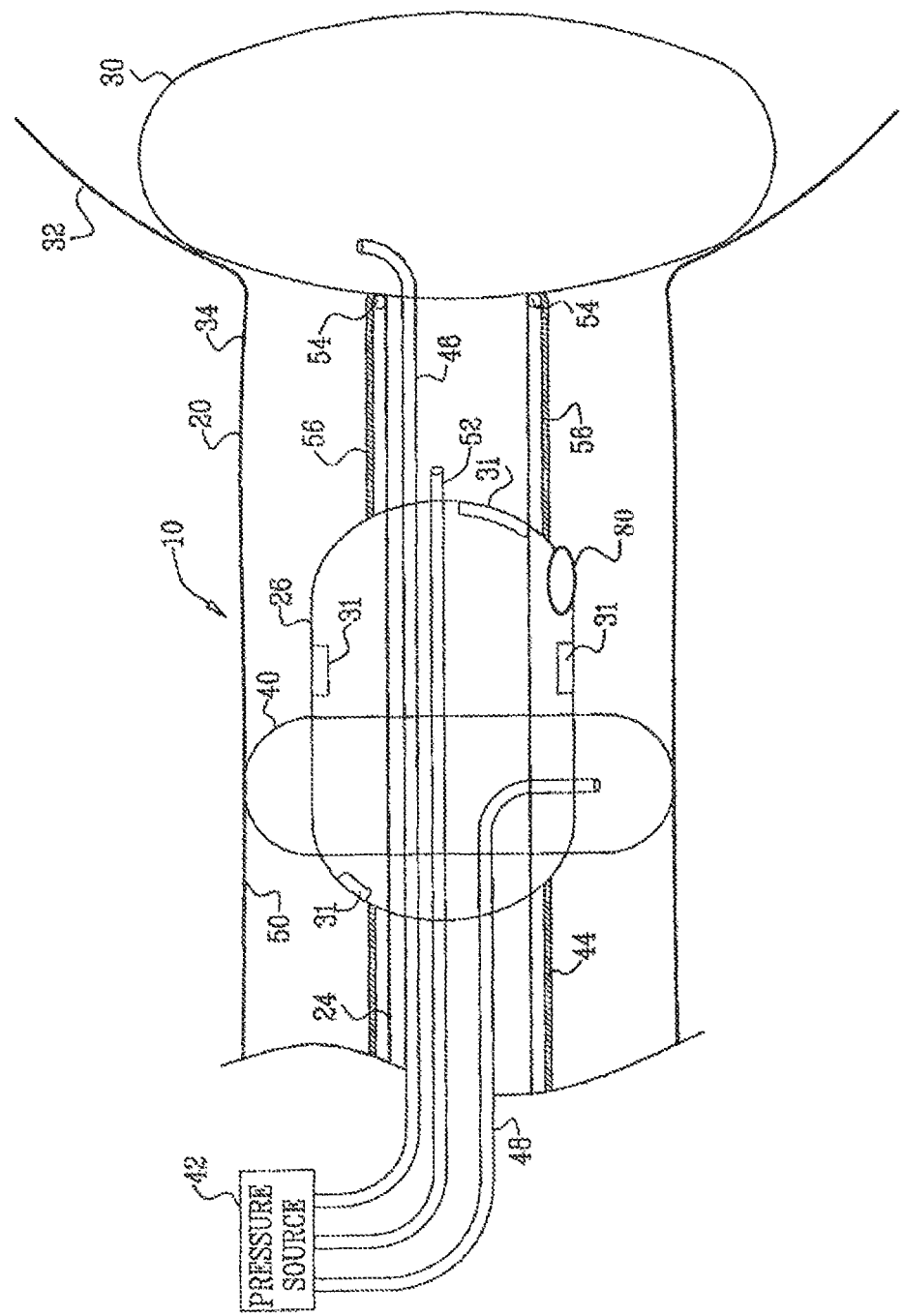
FIGS. 1 and 2 are schematic illustrations of an imaging system configured to be inserted into an esophagus of a subject, in accordance with an embodiment of the present invention.
Figure 2:
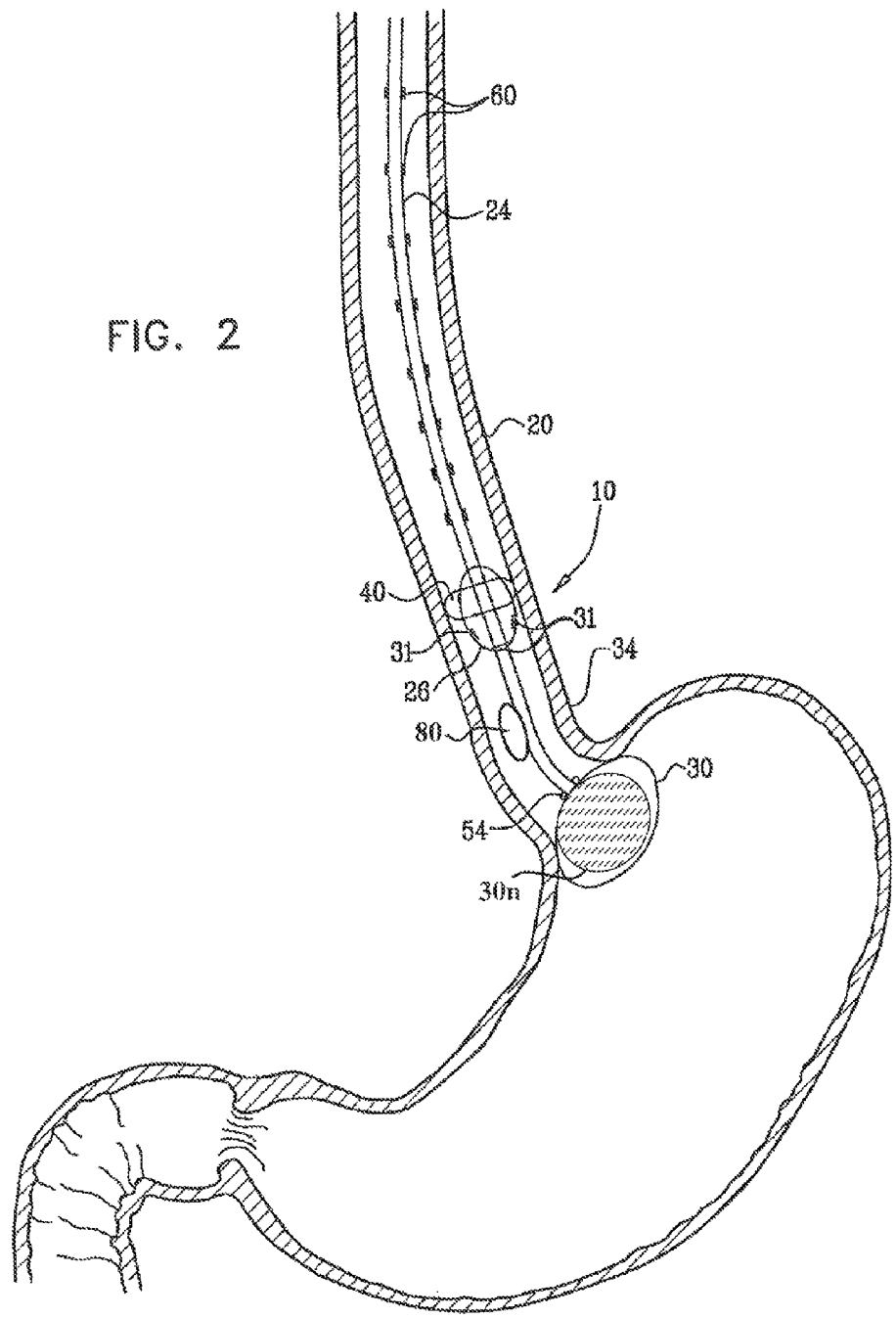

FIGS. 1 and 2 are schematic illustrations of an imaging system 10 configured to be inserted into an esophagus 20 of a subject, in accordance with an embodiment of the present invention. System 10 comprises an elongate carrier 24, an imaging capsule 26 configured to travel along the carrier, and an inflatable anchoring member 30 coupled to a distal end of carrier 24. Imaging capsule 26 comprises at least one imaging element 31, which is configured to image esophagus 20. Anchoring member 30 is inserted via esophagus 20 to a site in a stomach 32 in a vicinity of a lower esophageal sphincter (LES) 34, and inflated so as to anchor the distal end of carrier 24.

Imaging capsule 26 and anchoring member 30 are typically advanced distally through esophagus 20 by positioning the imaging capsule at a distal end of carrier 24 near the anchoring member, and pushing on carrier 24 until anchoring member 30 reaches stomach 32. Alternatively, carrier 24 and anchoring member 30 are first advanced through esophagus 20, and a tube 44 is used to push imaging capsule 26 over the inserted carrier. (Tube 44 may be larger than as shown in FIG. 1, and, for some applications, may surround carrier 24.)

In an embodiment of the present invention, elongate carrier 24 comprises a plurality of tubes and communication wires. An interior of anchoring member 30 is, in an embodiment, in fluid communication with a pressure source 42 via an anchoring member fluid supply tube 46. Pressure source 42 provides a pressurized biologically-compatible fluid, such as but not limited to, a source of pressurized air, $CO_2$, or water, in order to inflate anchoring member 30.

In an embodiment of the present invention, imaging capsule 26 comprises an inflatable piston head 40. The piston head is configured to be inflated in response to pressure from fluid pressure source 42 delivered via a piston fluid supply tube 48. Once inflated, piston head 40 forms a pressure seal with a wall 50 of esophagus 20. Piston head 40 comprises a medically-safe elastomeric material, such as polyurethane or silicone rubber. Piston head 40 is configured to travel proximally (i.e., towards the mouth) through esophagus 20 in response to pressure from fluid pressure source 42 delivered, via an advancement fluid supply tube 52, to a volume of esophagus 20 between piston head 40 and anchoring member 30. Alternatively, imaging capsule 26 is withdrawn proximally using tube 44.

Imaging element 31 comprises a camera (e.g., CCD or CMOS), or an x-ray, ultrasonic, MRI, infrared, microwave imaging device, or another sensor configured to perform an optical biopsy of the esophagus. For some applications, imaging element 31 comprises one or more lenses configured to enable forward and omnidirectional viewing, and/or means for illuminating the esophagus. For example, techniques may be used that are described in U.S. Provisional Patent Application 60/571,438, filed May 14, 2004, and/or International Patent Application PCT/IL2005/000500, filed May 11, 2005, both of which are assigned to the assignee of the present application and are incorporated herein by reference. Alternatively or additionally, imaging element 31 is positioned to enable viewing in a proximal direction.

In an embodiment of the present invention, system 10 comprises one or more pulleys 54, which enable imaging capsule 26 to be pulled distally via wires 56. This embodiment may be practiced in addition to the use of a piston head, as described, or, alternatively, without the use of a piston head.

In an embodiment of the present invention, carrier comprises a plurality of markers 60 that enable an operator of system 10 to visually determine a depth of imaging capsule 26 in the esophagus from the patient's teeth. Alternatively or additionally, the operator may view the markers using imaging element 31.

Although piston head 40 has been described in embodiments of the present invention as being in direct contact with wall 50 of esophagus 20, the scope of the invention includes establishing contact between the piston head and the wall of the esophagus through an intermediary, such as a sheath surrounding the piston head.

Figure 3:
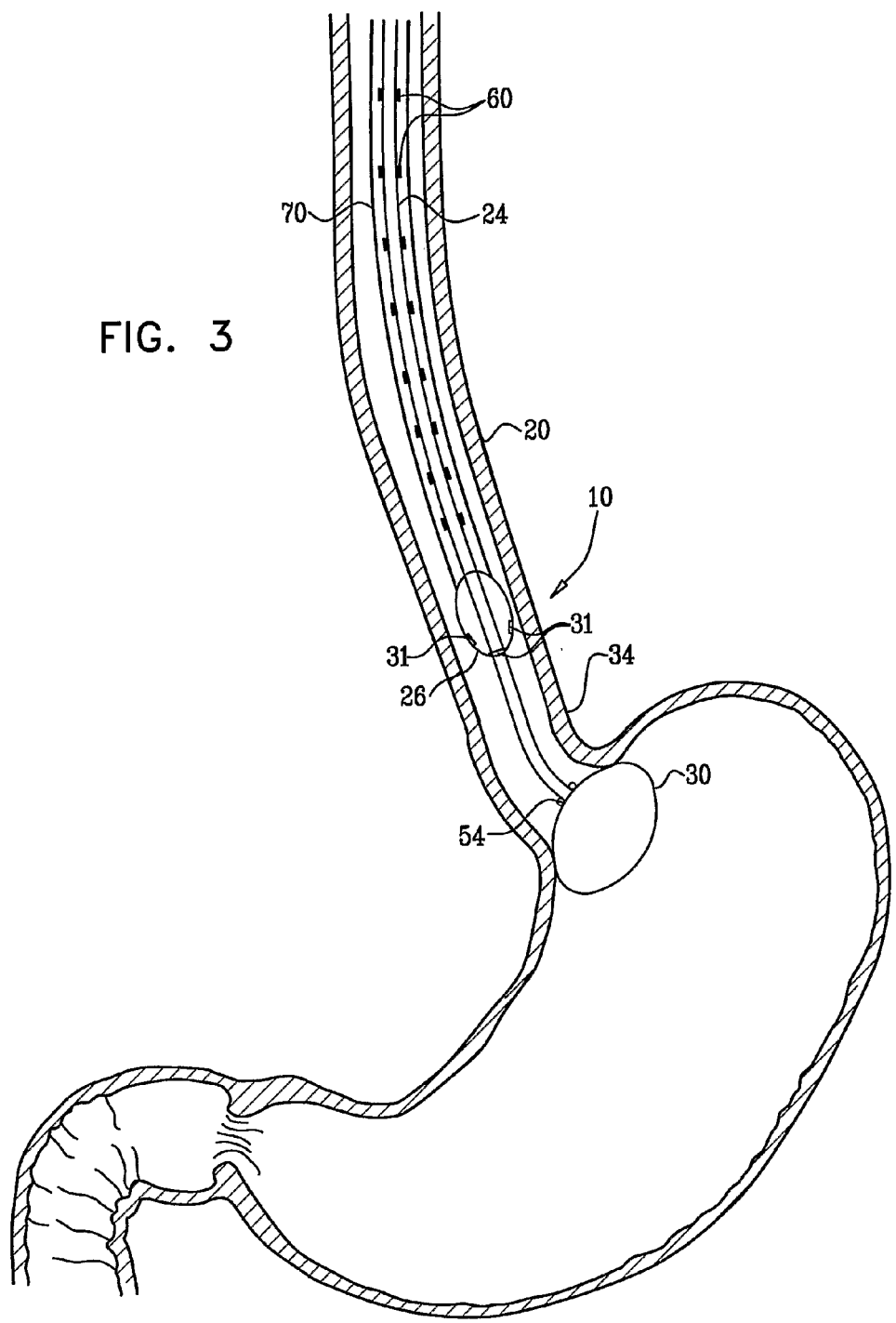
FIG. 3 is a schematic illustration of the imaging system of FIG. 1, in accordance with another embodiment of the present invention.

FIG. 3 is a schematic illustration of imaging system in accordance with an embodiment of the present invention. In the embodiment shown in FIG. 3, piston head 40 (FIG. 2) is not utilized. Instead, imaging capsule 26 is attached to a tube 70 that typically surrounds carrier 24. Tube 70 is free to advance and withdraw capsule 26. Capsule 26, in turn, is free to move proximally or distally with respect to carrier 24. In this manner, carrier 24 serves as a monorail, which is inserted into the esophagus at the beginning of a procedure, and maintained in place by anchoring member 30.

While anchoring member 30 is inflatable in accordance with some embodiments of the present invention, for some applications other techniques known in the art for stabilizing a tool in the gastrointestinal tract are used in order to maintain the position of member 30 near the lower esophageal sphincter.

In an embodiment, system 10 comprises a sample collection unit 80, shown in FIG. 1 in capsule 26 and in FIG. 2 as not an integral portion of the capsule, which is configured to collect a tissue or fluid sample from the esophagus. For example, the collection unit may use suction to pull tissue into a collection compartment, whereupon the tissue is excised by a cutting instrument. The excised tissue is maintained within the collection unit, and, typically, a portion of the collection unit closes in order to maintain separation of the excised tissue from the surrounding environment. The closure of the collection unit and excision of the tissue may, for some applications, be accomplished by the cutting instrument, which is typically activated by an actuator under physician control. Alternatively, a suitably-instrumented mechanical arm extends from the collection unit and retrieves a sample for biopsy.

Upon completion of the procedure, the collection unit is typically withdrawn proximally. For some applications, the collection unit performs analysis (e.g., chemical or optical analysis) of collected samples in situ, such as using techniques known in the art, and, typically, transmits information to a site outside of the patient's body. For example, the information may include raw data or results of analysis, and may be transmitted over wires or wirelessly.

In an embodiment, system 10 applies a drug to a site of the esophagus, in response to or independently of data retrieved or samples collected by system 10.

The scope of the present invention includes embodiments described in the following applications, all of which are assigned to the assignee of the present application and are incorporated herein by reference. In an embodiment, techniques and apparatus described in one or more of the following applications are combined with techniques and apparatus described herein.

US Patent Application Publication 2005/0154355 to Gross et al.

US Patent Application Publication 2004/0102681 to Gross

US Patent Application Publication 2005/0036059 to Goldwasser

US Patent Application Publications 2005/0038318 and 2005/0038319 to Goldwasser

US Patent Application Publication 2005/0038335 to Gross et al.

US Patent Application Publication 2005/0154278 to Cabiri et al.

PCT Publication WO 05/065044 to Cabiri et al.

U.S. patent application Ser. No. 10/967,922 to Cabiri et al., filed Oct. 18, 2004, entitled, "Pressure-propelled system for body lumen"

U.S. patent application Ser. No. 10/523,578 to Gross et al., filed Jan. 28, 2005, entitled, "Self-propelled imaging system"

U.S. Provisional Patent Application 60/571,438 to Dotan et al., filed May 14, 2004, entitled, "Omnidirectional and forward-looking imaging device"

U.S. Provisional Patent Application 60/607,986 to Cabiri et al., filed Sep. 8, 2004, entitled, "Mechanical aspects of pressure-propelled system for body lumen"

U.S. Provisional Patent Application 60/642,245, filed Jan. 6, 2005, entitled, "Gastrointestinal tool over guidewire"

International Patent Application PCT/IL2005/000178 to Goldwasser et al., filed Feb. 10, 2005, entitled, "Gastrointestinal tool over guidewire"

U.S. Provisional Patent Application 60/652,049 to Goldwasser et al., filed Feb. 10, 2005, entitled "Advanced techniques for gastrointestinal tool with guiding element"

U.S. Provisional Patent Application 60/680,074 to Degtiar et al., filed May 11, 2005, entitled, "Disposable endoscope connector"

an international patent application to Dotan et al., filed May 11, 2005, entitled, "Omnidirectional and forward-looking imaging device"

U.S. patent application Ser. No. 10/753,424 to Gross et al., entitled, "Pressure-propelled system for body lumen," filed Jan. 9, 2004

U.S. Provisional Patent Application 60/704,656 to Goldwasser et al., entitled, "Tools for use in esophagus," filed Aug. 1, 2005 a PCT patent application to Degtiar et al., entitled, "Disposable endoscope connector," filed May 11, 2006 a PCT patent application to Cabiri et al., entitled, "Endoscopic measurement techniques," filed May 11, 2006 a PCT patent application to Goldwasser et al., entitled, "Tools for use in small intestine," filed on even date herewith.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for imaging the esophagus of a subject, comprising:

an anchor member comprising an inflatable anchor member so dimensioned as to have a lateral diameter less than the diameter of the lower esophageal sphincter (LES) of the subject when deflated and having a lateral diameter greater than the diameter of the LES of the subject when inflated, said anchor member being configured to pass through the LES of the subject into the subject's stomach and form a pressure seal with the LES upon inflation thereof;

an elongate carrier, configured to be advanced through the esophagus of the subject to the stomach of the subject, and comprising an anchor fluid supply tube, the distal end of which extends into the anchor member for supplying fluid pressure from a fluid pressure source to inflate the anchor member;

an imaging capsule, configured to move along the carrier when the anchor member is in the vicinity of the LES;

a piston head coupled to the imaging capsule configured to form a pressure seal with a wall of the esophagus upon inflation thereof to thereby allow moving the imaging capsule along the carrier in response to fluid pressure applied to a volume of the esophagus external to the apparatus between the piston head and the anchor member, said piston head being configured to travel proximally through the esophagus from the LES to the mouth of the subject in response to pressure from a fluid pressure source delivered to the volume of the esophagus between said piston head and said anchor member; and a fluid supply tube for supplying fluid pressure to the volume of the esophagus between said piston head and said anchor member when in use.

2. The apparatus according to claim 1, wherein the imaging capsule comprises a sample collection unit, configured to retrieve a sample fluid or tissue of the esophagus by at least one of suction and a cutting instrument provided via an opening provided therein.

3. The apparatus according to claim 1, wherein the apparatus comprises a sample collection unit coupled to the carrier and not an integral portion of the imaging capsule, wherein the collection unit is configured to sample fluid or tissue of the esophagus.

4. The apparatus according to claim 1, wherein the imaging capsule is shaped to define a bore thereof, and wherein the carrier is configured to pass through the bore to allow the imaging capsule to move with respect to the carrier.

5. The apparatus according to claim 1, wherein
the imaging capsule is configured to travel along the carrier, and wherein the imaging capsule comprises:
an optical imaging element.

6. The apparatus according to claim 5, wherein the imaging capsule comprises a sample collection unit, configured to retrieve a sample fluid or tissue of the esophagus by at least one of suction and a cutting instrument provided via an opening provided therein.

7. The apparatus according to claim 5, wherein the apparatus comprises a sample collection unit coupled to the carrier and not an integral portion of the imaging capsule, wherein the collection unit is configured to sample fluid or tissue of the esophagus.

8. The apparatus according to claim 1, comprising at least one wire configured to move the imaging capsule with respect to the carrier when the anchor member is in the vicinity of the LES.

9. The apparatus according to claim 8, comprising one or more pulleys to facilitate movement of the imaging capsule along the carrier via the at least one wire.

10. The apparatus according to claim 1, comprising a tube for moving the imaging capsule with respect to the elongate carrier.

11. A method for imaging the esophagus of a subject using the apparatus of claim 1, comprising:
advancing said elongate carrier through an esophagus of a subject;
mounting in the stomach of the subject in the vicinity of the lower esophageal sphincter (LES) of the subject said anchor member that is coupled to the distal end of said carrier; and
moving said imaging capsule with respect to said carrier when said anchor member is in the vicinity of the LES.

12. The method according to claim 11, wherein said imaging capsule applies a treatment to the esophagus.

13. The method according to claim 11, wherein the imaging capsule comprises a sample collection unit, configured to retrieve a sample fluid or tissue of the esophagus by at least one of suction and a cutting instrument provided via an opening provided therein, and further comprising comprising sampling fluid or tissue of the esophagus by the sample collection unit of the imaging capsule.

14. The method according to claim 11, wherein the imaging capsule is shaped to define a bore thereof, and comprising placing the elongate carrier within the bore of the imaging capsule.

15. The method according to claim 11, wherein mounting the anchor member comprises inflating the anchor member when it is in the stomach.

16. The method according to claim 11, wherein mounting the anchor member comprises expanding the anchor member when it is in the stomach.

* * * * *